United States Patent
Schoppmann et al.

(10) Patent No.: US 10,309,911 B2
(45) Date of Patent: Jun. 4, 2019

(54) DEVICE AND METHOD FOR RADIOSCOPIC EXAMINATION OF A STRIP-SHAPED MATERIAL HAVING A SUBSTANTIAL COMPONENT OF RUBBER OR PLASTICS

(71) Applicant: TROESTER GmbH & Co. KG, Hannover (DE)

(72) Inventors: Kurt Schoppmann, Hannover (DE); Bernd Pielsticker, Wunstorf (DE)

(73) Assignee: TROESTER GMBH & CO. KG, Hannover (DE)

( * ) Notice: Subject to any disclaimer, the term of this patent is extended or adjusted under 35 U.S.C. 154(b) by 333 days.

(21) Appl. No.: 15/250,948

(22) Filed: Aug. 30, 2016

(65) Prior Publication Data

US 2017/0059495 A1   Mar. 2, 2017

(30) Foreign Application Priority Data

Sep. 2, 2015 (DE) .................. 10 2015 114 658

(51) Int. Cl.
  *G01N 23/16* (2018.01)
  *G01N 23/18* (2018.01)
  *G01N 33/44* (2006.01)
  *G01N 23/087* (2018.01)

(52) U.S. Cl.
  CPC ......... *G01N 23/185* (2013.01); *G01N 23/087* (2013.01); *G01N 23/16* (2013.01); *G01N 23/18* (2013.01); *G01N 33/445* (2013.01); *G01N 2223/627* (2013.01); *G01N 2223/642* (2013.01); *G01N 2223/643* (2013.01); *G01N 2223/646* (2013.01); *G01N 2223/652* (2013.01)

(58) Field of Classification Search
  CPC .. G01N 23/16; G01N 23/18; G01N 2223/642; G01N 2223/643; G01N 2223/645; G01N 2223/646; G01N 2223/652
  See application file for complete search history.

(56) References Cited

U.S. PATENT DOCUMENTS

| 4,534,248 A | 8/1985 | Andersson |
| 4,587,667 A | 5/1986 | Osmont et al. |
| 4,707,887 A | 11/1987 | Leifeld et al. |

(Continued)

FOREIGN PATENT DOCUMENTS

| DE | 971619 C | 2/1959 |
| DE | 1690098 A1 | 4/1971 |

(Continued)

*Primary Examiner* — Thomas R Artman
(74) *Attorney, Agent, or Firm* — Leydig, Voit & Mayer, Ltd.

(57) ABSTRACT

A device and method for the radioscopic examination of a continuous strip-shaped material of rubber which runs continuously in particular. During the movement, the strip-shaped material is x-rayed by a radioscopic measurer and the entire cross-sectional surface is detected so that foreign bodies or defects present in the material are detected according to their position and orientation. An elimination device removes the previously identified foreign body during the feed movement of the material in that a tool, configured as a punching tool, of the elimination device is moved synchronously with the material.

18 Claims, 2 Drawing Sheets

(56) References Cited

U.S. PATENT DOCUMENTS

| | | | |
|---|---|---|---|
| 6,885,198 B2* | 4/2005 | Dueholm | G01B 15/025 |
| | | | 324/639 |
| 8,829,459 B2* | 9/2014 | Ichizawa | G01N 23/16 |
| | | | 250/375 |
| 2003/0137288 A1* | 7/2003 | Dueholm | G01B 15/025 |
| | | | 324/71.3 |
| 2010/0119038 A1* | 5/2010 | Suyama | G01N 23/04 |
| | | | 378/57 |
| 2011/0147603 A1* | 6/2011 | Ichizawa | G01N 23/16 |
| | | | 250/375 |
| 2013/0136816 A1 | 5/2013 | Kuesel et al. | |
| 2017/0059495 A1* | 3/2017 | Schoppmann | G01N 23/087 |

FOREIGN PATENT DOCUMENTS

| | | |
|---|---|---|
| DE | 3034543 A1 | 4/1982 |
| DE | 3436498 A1 | 4/1986 |
| DE | 19607582 A1 | 9/1997 |
| DE | 10160398 B4 | 11/2004 |
| DE | 102009012588 A1 | 11/2009 |
| DE | 102010036637 A1 | 2/2012 |
| EP | 1318377 A1 | 6/2003 |

\* cited by examiner

DEVICE AND METHOD FOR RADIOSCOPIC EXAMINATION OF A STRIP-SHAPED MATERIAL HAVING A SUBSTANTIAL COMPONENT OF RUBBER OR PLASTICS

CROSS-REFERENCE TO RELATED APPLICATIONS

Priority is claimed to German Patent Application No. DE 10 2015 114 658.4, filed on Sep. 2, 2015, the entire disclosure of which is hereby incorporated by reference herein.

FIELD

The invention relates to a radioscopic device.

BACKGROUND

In modern tire production, digital radioscopy has already been frequently used in non-destructive testing and thus belongs to the prior art due to prior public use.

In this respect, material testing is carried out in the form of sampling inspection, or material testing is directly incorporated into the production process. Particularly strict requirements are imposed on tire production which can consist of more than 200 different materials and is subject to high quality requirements.

The typical testing objective of x-ray testing mainly comprises detecting the symmetry of the inner tire structure. In this respect, the layer offset of individual belts, the steel cord layers and also the cord spacings in the carcass are examined. Furthermore, the tires are examined for bodies of air and foreign bodies or inclusions of flaws. In this respect, an x-ray image of the entire tire can be generated by rotation.

The ASTM Standard F-1035 is used, for example to qualify the image quality for radioscopic systems for tire testing. This standard uses a flat disc of a defined rubber mixture, in which a plurality of materials is introduced in specific structures and which can be respectively differentiated in the x-ray image.

DE 196 07 582 A1 discloses a method for monitoring an extruded strip. Here, x-rays are continuously or gradually passed through small regions of the strip transversely to the plane of the strip and the type, size, shape and/or distribution of the contaminants are detected inside the strip and also on the surface of the strip. If the contaminants exceed a predetermined threshold value, the dispersed system is excluded from being further processed.

DE 971 619 B discloses a system for wall inspection during the production of plastics tubes and pipes using radioactive radiators.

DE 101 60 398 B4 relates to a method for examining a matting, moved by a conveying means, of biomass particles, in particular of fibers or woodchips, for the production of chipboard. The biomass particles are spread by a spreading machine onto a forming belt. The precompressed matting then passes through an examining device, equipped with radiation sources, for radiographing the matting which is thus examined for foreign bodies such as metal parts or plastics parts. The forming belt is divided and, if a defect is found in the matting by the examining device, the belt can be moved apart with the formation of a gap so that the portion of the matting containing the defect is disposed of in a discharge shaft.

DE 10 2009 012 558 A1 relates to an examination device of a production machine of a filling plant. To exclude the presence of foreign bodies in the filled cans, the separated and packaged cans are examined by an x-ray examination device.

In practice, if a foreign body is detected in the material, the material feed is interrupted so that a portion of material which includes the foreign body or defects can be removed manually. The material feed and thereby the subsequent processing procedures of the material are interrupted thereby and additional start-up measures are required to continue the process.

SUMMARY

An aspect of the invention provides a device, comprising: a radioscopic measurer configured to examining a strip-shaped material which includes a rubber, plastic, or mixture of two or more of any of these, the measurer being configured to detect an entire cross-sectional surface so that one or more foreign bodies or defects present in the material can be detected in the material according to their size, position and/or orientation; and an eliminator configured to remove at least one of the foreign bodies or defects, based on acquired data, together with a partial region, the partial region including the at least one foreign body or defect, of the cross-sectional surface.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
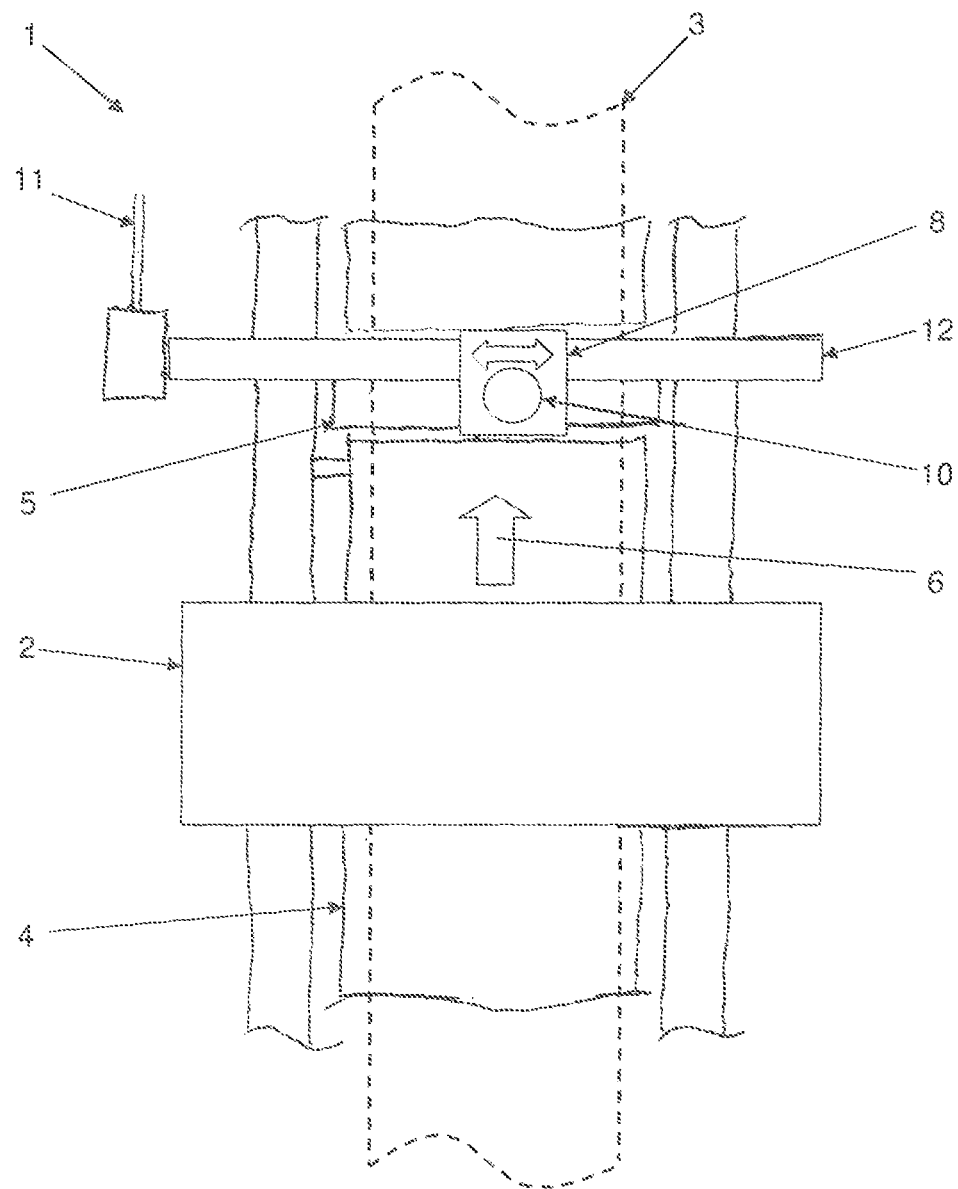
FIG. 1 is a plan view of a device according to the invention having an elimination device.

Proceeding from this background, an object of the invention is to make it possible to further improve the production process, particularly during the processing of strand-shaped or strip-shaped materials.

An aspect of to the invention provides a device having a radioscopic measuring means for examining a continuous strip-shaped material which in particular runs continuously and has a substantial component of rubber or plastics, it being possible for said material to be fed by a conveying means having a support which can be driven in a revolving manner. The invention also relates to a method for the radioscopic examination of the material.

Thus, according to the invention, the measuring means in the device is configured to detect or x-ray the entire cross-sectional surface so that it is possible to detect foreign bodies or defects present in the material including possible contaminants as well as material characteristics or material parameters which differ from set values according to their size, position and/or orientation in the material and that the device is fitted with an elimination device for removing the foreign body or the defect, or alternatively or in addition is fitted with a marking device for marking the foreign body or the defect based on the position data together with a partial region of the cross-sectional surface which includes the foreign body or the defect. As a result, in a particularly advantageous manner a detected foreign body or a defect in the material is not only detected, but immediately removed, in particular while the material is being moved continuously by the conveying means which has a support which can be driven in a revolving manner. For this purpose, not only is the position determined in the longitudinal and transverse directions, i.e. the distance from the side edges. In fact, the depth coordinates of the foreign body or of the defect are also determined in the cross-sectional plane, so that the partial region which is to be removed can be restricted locally in an optimum manner. Starting from an upper side or lower side, subject to the detected distance from the surface of the strip-shaped material, the partial region is raised and removed preferably not as a break-through in the material, but being confined to necessary planes. Tong-like or scissor-like tools for example are suitable for this purpose. The loss of material associated therewith is thus reduced to a minimum, in that the material volume of the partial region is not comprised by the entire material thickness, but is restricted to a layer which is preferably close to the surface.

In this respect, it has proved to be particularly practical if the elimination device removes the partial region during a feed movement of the material. For this purpose, at least one separating tool of the elimination device is moved together with the material, particularly in connection with the conveying means during the separating procedure of the partial region. As a result, undesirable tensions and deformations in the material can be avoided.

A particularly advantageous embodiment of the present invention is also achieved in that the elimination device has at least one punching tool for punching out the partial region. A hollow-cylindrical punching tool is particularly suitable here, which is fitted with a holding means enclosed by the punching tool. The holding means is used to temporarily fix the partial region by applying a contact pressure which can also be adjusted, if required. Serving as an abutment is a support, which is stationary or movable together with the conveyor belt, of the conveying means which is configured for example as a conveyor belt or as a modular belt. The feed movement of the punching tool is preferably performed by means of a threaded spindle or a hydraulic or pneumatic positioning means with respect to an upper side or lower side of the strip of material and preferably takes place in a path-controlled manner such that layers located below or above the foreign body or defect are not affected by the engagement of the tool, or are only slightly affected. As soon as the punching tool has reached the predetermined set position as the set depth in the material cross section, it can be set at the same time into a revolving or reversing rotational movement about the infeed axis to thus optimize the separation of the partial region of the material. Of course, the device is not restricted to a single punching tool. In fact, different punching tools of different sizes can be used. Likewise, punching tools which can be adjusted in diameter can be realized for optimum adaptation to the foreign body or defect.

A further likewise particularly advantageous modification of the invention is also achieved in that the elimination device has a counterholder which is arranged inside the punching tool in the partial region to be removed, which can be applied against a surface of the material and which has a contact surface by which the partial region, separated from the material, can be fixed and which at the same time has a construction suitable for transporting and removing the partial region. For this purpose, the contact surface can have projections which can be introduced into the surface of the partial region and by which a detachable mechanical clamping is achieved by a non-positive or positive connection or by adhesion. The partial region can thus be easily transported to a disposal station.

Furthermore, it is particularly practical if the elimination device is movable together with the transporting means particularly in a translatory manner in the direction of the main extension plane of the material in mutually perpendicular axes. Suitable for this purpose is, for example, an elimination device in a portal construction which spans the strip of material or the conveying means. Alternatively, the elimination device can also be fitted with a swivel arm for the punching tool.

A particularly preferred modification of the invention is achieved in that the device has a means for measuring the density of the material, to thus be able to optimally control the punching tool, subject to the acquired measured values. Furthermore, the density measurement is also used to detect defects in the material based on a density which differs from a set value, with other material parameters being unchanged. Otherwise, these can result in inhomogeneous characteristics in a subsequent product and are therefore also removed like foreign bodies by the elimination device according to the invention.

Furthermore, it is advantageous if the device has a means for measuring the material thickness in the cross-sectional plane, so that the partial region to be removed can be calculated such that a break-through in the material can be substantially avoided.

Before the foreign body is removed, the coordinates of the foreign body or of the defect are preferably detected in the main extension plane and/or in the cross-sectional plane of the material. As a result, it is possible to restrict the partial region to be removed to a necessary minimum, in that the depth from an upper or a lower surface of the material and also the peripheral distance from at least one lateral edge are detected.

The object according to the invention is further achieved by a method for the radioscopic examination of a material which is fed particularly continuously by a conveying means and which has a substantial component of rubber or plastics, in that the entire cross-sectional surface of the material is x-rayed and foreign bodies or defects which are present in the material are thus detected and separated from the rest of the material by an elimination device together with a partial region, which includes the foreign body or defects, of the cross-sectional surface. Consequently, it is possible for the first time to remove foreign bodies or defects in a targeted manner from the material, without the strand of material having to be interrupted for this purpose. Instead, in the partial region merely a volume of the material is removed which is only slightly larger than the foreign body. In this respect, even the contour of the foreign body or of the defect can be considered and the cutting guidance can be coordinated accordingly during the removal of the foreign body or defect. Thereafter, the material is delivered, preferably without any interruptions, to a feed opening of an extruder.

The object according to the invention is further achieved by a method for the radioscopic examination of a material, in that the density is determined by a dual x-ray absorptiometry method or by a dual energy method, and the measured values obtained thus are used to control or regulate a subsequent extrusion process to which the material is delivered. The use of a dual x-ray absorptiometry method which is known per se can reliably determine the composition of the material and in particular the density thereof. For this purpose, two photographs are taken using different x-ray energy. A comparison of the two measurements makes it possible to determine the density in any desired material regions or in the entire material.

The density can also be determined by a simple radioscopic examination and by a density measurement along the cross-sectional plane. The determination of the cross section can also be used to control or regulate a subsequent extrusion process. The determined cross section and the feed rate of the material strip can furthermore be used to detect the wear of the extruder based on the extrusion parameters (rotational speed, temperature, pressure, pin configuration, material characteristics, screw geometry, inter alia).

Fig. Fig. The device 1 according to the invention having a radioscopic measuring means 2 is described in more detail below with reference to FIGS. 1 and 2. The device 1 is used to examine a continuously running strip-shaped material 3 made of rubber. A conveying means 4 which is configured as a conveyor belt is used to feed the material, the support 5 thereof which can be driven in a revolving manner, transporting the material 3 in the arrow direction 6 and delivering it to a feed opening (not shown) of an extruder for further processing. During the movement, the strip-shaped material 3 is x-rayed by the radioscopic measuring means 2 and the entire cross-sectional surface is detected so that foreign bodies 7 or defects present in the material 3 are detected according to their position and orientation. A single exposure to rays is adequate to detect the entire cross section. Furthermore, the device 1 is fitted with an elimination device 8 for removing the previously identified foreign body 7 or defect using the determined coordinates together with a partial region 9 which includes the foreign body 7 or the defect, based on the main extension plane and on the cross-sectional surface of the material 3. The elimination device 8 allows this partial region 9 to be removed during the feed movement of the material 3 in that the tool 10, configured as a punching tool, of the elimination device 8 is accordingly moved synchronously by appropriate guides 11, 12 in the feed direction and also in the transverse direction thereto.

Figure 2:
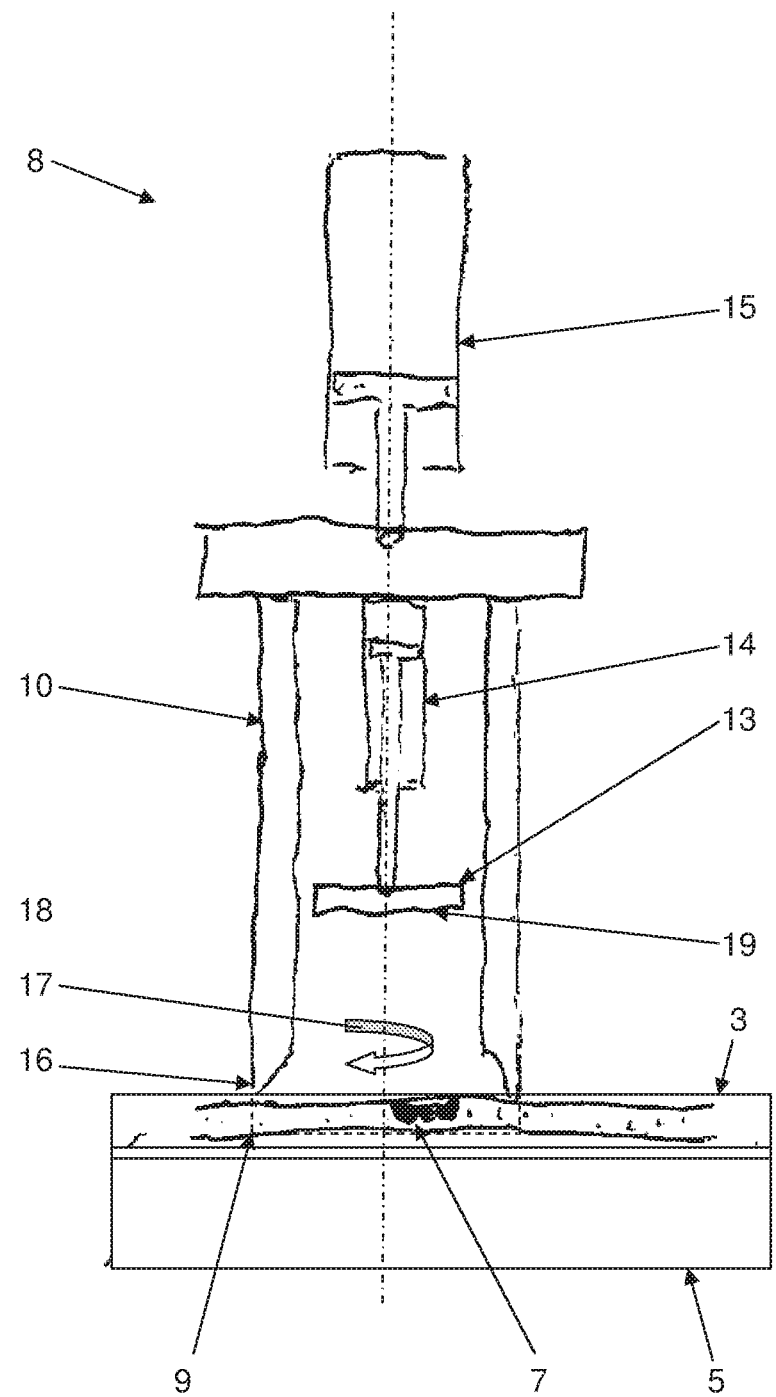
FIG. 2 is a side view of the elimination device.

The elimination device 8 shown in a side view in FIG. 2 with the hollow-cylindrical tool 10 encloses on the peripheral side a counterholder 13 which can be pretensioned with respect to the material 3. To remove the partial region 9, first of all the counterholder 13 is lowered onto the material 3 by a piston 14 and the material is pressed by the counterholder against the support 5 of the jointly running conveying means 4. Thereafter, the tool 10 is lowered in a path-controlled manner by a further piston 15 until a cutting edge 16 has reached the material plane of the incorporated foreign body 7. Overlapping with the feed or subsequently thereto, the counterholder 13 and the tool 10 perform a rotational movement 17 about the infeed axis 18, by which the partial region 9 is then separated from the rest of the material 3. To be able to dispose of the separated partial region 9, the counterholder 13 is fitted on the outside with a contact surface 19 which has a structuring and on which the punched out partial region 9 temporarily adheres and can thereby be easily delivered to a disposal means.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

LIST OF REFERENCE NUMERALS

1 Device
2 Measuring means
3 Material
4 Conveying means
5 Support
6 Arrow direction
7 Foreign body
8 Elimination device
9 Partial region
10 Tool
11 Guide
12 Guide
13 Counterholder
14 Piston
15 Piston
16 Cutting edge
17 Rotational movement
18 Infeed axis
19 Contact surface

The invention claimed is:

1. A device, comprising:
a radioscopic measurer configured to examine an entire cross-sectional surface of a strip-shaped material which includes a rubber, plastic, or mixture of two or more of any of these so as to detect coordinates of one or more foreign bodies or defects present in the material at a depth from an upper or lower surface of the material and at an edge distance from at least one lateral edge of the material; and
an eliminator configured to remove at least one of the foreign bodies or defects together with a partial region including the at least one foreign body or defect without breaking through the cross-sectional surface of the material.

2. The device of claim 1, wherein the radioscopic measurer is configured to examine a continuous strip-shaped material.

3. The device of claim 1, wherein the radioscopic measurer is configured to examine a material that consists of a rubber, a plastic, or a mixture of two or more of these.

4. The device of claim 1, wherein the eliminator is configured to remove the partial region during a feed movement of the material.

5. The device of claim 1, wherein the eliminator includes a tool configured to separate the partial region.

6. The device of claim 1, wherein the eliminator includes more than one tool configured to separate the partial region.

7. The device of claim 1, wherein the eliminator includes a punching tool configured to separate the partial region.

8. The device of claim 1, wherein the eliminator includes a counterholder,
wherein the counterhold is arranged in the partial region to be removed,
wherein the counterhold can be applied against a surface of the material, and
wherein the counterhold includes a contact surface by which the partial region can be fixed before and/or after it has been separated.

9. The device of claim 1, wherein the eliminator is movable synchronously with the material.

10. The device of claim 9, wherein the eliminator is movable in a translatory manner.

11. The device of claim 1, further comprising:
a density measurer suitable for the material.

12. The device of claim 1, further comprising:
a thickness measurer configured to measure thickness of the material in the cross-sectional plane of the material.

13. The device of claim 1, wherein the eliminator includes a punching tool having a path-controlled feed movement such that layers located above or below the at least one foreign body or defect are not affected by engagement of the tool.

14. The device of claim 1, wherein the eliminator includes a punching tool configured to be moved to and rotate at a set depth in the material so as to remove the partial region.

15. A method for radioscopically examining a material including a rubber, plastic, or mixture of two or more of any of these, the method comprising:
x-raying an entire cross-sectional surface of the material so as to detect coordinates of one or more foreign bodies and/or defects present in the material at a depth from an upper or lower surface of the material and at an edge distance from at least one lateral edge of the material; and
separating at least one of the foreign bodies and/or defects from the material together with a partial region including the at least one foreign body or defect without breaking through the cross-sectional surface of the material.

16. The method of claim 15, wherein the material is continuously fed.

17. The method of claim 15, further comprising:
determining a density of the material using dual x-ray absorptiometry or dual energy, to obtain measured values; and
controlling or regulating a subsequent extrusion process using the measured values.

18. The method of claim 17, wherein the material is continuously fed.

* * * * *